(12) United States Patent
Chien et al.

(10) Patent No.: US 6,695,009 B2
(45) Date of Patent: Feb. 24, 2004

(54) MICROFLUIDIC METHODS, DEVICES AND SYSTEMS FOR IN SITU MATERIAL CONCENTRATION

(75) Inventors: Ring-Ling Chien, San Jose, CA (US); Benjamin N. Wang, Palo Alto, CA (US)

(73) Assignee: Caliper Technologies Corp., Mountain View, CA (US)

( * ) Notice: Subject to any disclaimer, the term of this patent is extended or adjusted under 35 U.S.C. 154(b) by 225 days.

(21) Appl. No.: 10/013,847

(22) Filed: Oct. 30, 2001

(65) Prior Publication Data

US 2002/0079008 A1 Jun. 27, 2002

Related U.S. Application Data

(60) Provisional application No. 60/244,807, filed on Oct. 31, 2000.

(51) Int. Cl.⁷ .......................... G05D 7/06; B01D 15/08
(52) U.S. Cl. ...................... 137/827; 137/13; 137/806; 137/818; 204/601
(58) Field of Search ................. 137/806, 828, 137/825, 827, 818, 14, 13; 204/601

(56) References Cited

U.S. PATENT DOCUMENTS

| | | | | |
|---|---|---|---|---|
| 4,908,112 A | * | 3/1990 | Pace | 356/318 |
| 5,089,099 A | | 2/1992 | Chien et al. | |
| 5,116,471 A | | 5/1992 | Chien et al. | |
| 5,126,022 A | * | 6/1992 | Soane et al. | 204/458 |
| 5,296,114 A | * | 3/1994 | Manz | 204/451 |
| 5,429,728 A | | 7/1995 | Gordon | |
| 5,599,432 A | * | 2/1997 | Manz et al. | 204/451 |
| 5,660,703 A | | 8/1997 | Dasgupta | |
| 5,800,690 A | * | 9/1998 | Chow et al. | 204/451 |
| 5,858,195 A | | 1/1999 | Ramsey | |
| 5,869,004 A | | 2/1999 | Parce et al. | |
| 5,948,227 A | | 9/1999 | Dubrow | |
| 5,955,028 A | | 9/1999 | Chow | |
| 6,004,515 A | | 12/1999 | Parce et al. | |
| 6,062,261 A | * | 5/2000 | Jacobson et al. | 137/827 |
| 6,213,151 B1 | * | 4/2001 | Jacobson et al. | 137/827 |
| 6,319,379 B1 | | 11/2001 | Davidson et al. | |
| 2002/0003089 A1 | | 1/2002 | DeVault | |

FOREIGN PATENT DOCUMENTS

WO     WO 01/63270     8/2001

OTHER PUBLICATIONS

Beckers, J.L. et al., "Sample staking in capillary zone electrophoresis: Principles, advantages and limitations," *Electrophoresis* (2000) 21:2747–2767.

Bharadwaj, R. et al., "Dynamics of field amplified sample stacking," *Proceedings of 2001 ASME International Mechanical Engineering Congress and Exposition* Nov. 11–16, 2001.

Breadmore, M.C. et al., "Approaches to enhancing the sensitivity of capillary electrophoresis methods for the determination of inorganic and small organic anions," *Electrophoresis* (2001) 22:2464–2489.

Chien, R. et al., "Multiport flow–control system for lab–on–a–chip microfluidic devices," *J. Anal. Chem.* (2001) 371:106–111.

(List continued on next page.)

*Primary Examiner*—A. Michael Chambers
(74) *Attorney, Agent, or Firm*—Matthew B. Murphy

(57) ABSTRACT

Methods of concentrating materials within microfluidic channel networks by moving materials into regions in which overall velocities of the material are reduced, resulting in stacking of the material within those reduced velocity regions. These methods, devices and systems employ static fluid interfaces to generate the differential velocities, as well as counter-current flow methods, to concentrate materials within microscale channels.

37 Claims, 5 Drawing Sheets

OTHER PUBLICATIONS

Kuldvee, R. et al., "Head column field–amplified stacking from the flow: Stabilization of the sample plug position by using bckpressure," *Electrophoresis* (2000) 21:2879–2885.

Palmer, J. et al., "Stacking neutral analytes in capillary electrokinetic chromatography with high–salt sample matrixes," *Anal. Chem.* (Apr. 2000) 72:1941–1943.

Palmer, J. et al., "Electrokinetic injection of stacking neutral analytes in capillary and microchip electrophoresis," *Anal. Chem.* (Feb. 2001) 73:725–731.

Quirino, J.P. et al., "Approaching a million–fold sensitivity increase in capillary electrophoreses with direct ultraviolet detection: cation–selective exhaustive injection and sweeping," *Anal. Chem.* (May 2000) 72:1023–1030.

Quirino, J.P. et al., "Strategy for on–line preconcentration in chromatographic separations," *Anal. Chem.* (Nov. 2001) 73:5539–5543.

Quirino, J.P. et al., "On–line preconcentration in capillary electrochromatography using a porous monolith together with solvent gradient and sample stacking," *Anal. Chem.* (Nov. 2001) 73:5557–5563.

Woolley, A.T. et al., "Ultra–high–speed DNA fragment separations using microfabricated capillary array electrophoresis chips," *PNAS* (1994) 91:11348–11352.

Yang, H. et al., "Sample stacking in laboratory–on–a–chip devices," *J. Chromatog.* (2001) 924:155–163.

Jacobson, S.C. et al., "Microchip electrophoresis with sample stacking," *E lectrophoresis* (1995) 16(4):481–486.

Kutter, J.P. et al., "Determination of Metal Cations in Microchip Electrophoresis Using On–Chip Complexation and Sample Stacking," *J. Microcolumn Separations* (1998) 10(4):313–319.

\* cited by examiner

MICROFLUIDIC METHODS, DEVICES AND SYSTEMS FOR IN SITU MATERIAL CONCENTRATION

CROSS REFERENCE TO RELATED APPLICATION

This application claims the benefit of U.S. provisional patent application No. 60/244,807, filed Oct. 31, 2000, the entire disclosure of which is hereby incorporated herein by reference in its entirety for all purposes.

BACKGROUND OF THE INVENTION

Microfluidic devices and systems have been developed that provide substantial advantages in terms of analytical throughput, reduced reagent consumption, precision of data, automatability, integration of analytical operations and miniaturization of analytical equipment. These devices and systems gain substantial benefits from operating within the microscale range where analyses are carried out on sub-microliter, and even sub-nanoliter quantities of fluid reagents. Because these systems operate on such small scales, they use substantially smaller amounts of precious reagents, are able to mix and react materials in much shorter time frames, can be performed in small integrated systems, e.g., that perform upstream and downstream operations, and are far more easily automated.

While microfluidic devices and systems have a large number of substantial advantages, the one area where they suffer from a distinct disadvantage over conventional scale analyses is where a material to be analyzed is only present at very low concentrations. Specifically, where an analyte in a sample is at a very low concentration, very small volumes of the material will contain only very small amounts of the analyte of interest. Often, these amounts of analyte may fall near or below the detection threshold for the analytical system. In conventional scale operations, material can be provided in much larger volumes and substantially concentrated prior to analysis, using conventional concentration methods. These conventional concentration methods, however, do not lend themselves to microscale quantities of material.

Accordingly, it would be desirable to be able to provide methods, devices and systems that operate in the microfluidic domain, but that are able to perform a concentration operation to substantially concentrate an analyte of interest in on a sample material. The present invention meets these and a variety of other needs.

SUMMARY OF THE INVENTION

In a first aspect, the present invention provides a method of concentrating a material, comprising, providing at least first and second channel portions. The second channel portion intersects and is in fluid communication with the first channel portion. The first channel portion has at least first and second fluid regions. The first fluid region comprises the material and has a conductivity that is lower than the second fluid. The first and second fluids are in contact at a first substantially static interface. An electric field is applied through the first and second fluid regions in the first channel portion to concentrate the material at the first substantially static interface.

Another aspect of the present invention is a method of concentrating a material, comprised of providing a first channel portion having at least first and second fluid regions. The material has a first electrophoretic velocity in the first fluid region and a second electrophoretic velocity in the second fluid region. The second electrophoretic velocity is less than the first electrophoretic velocity as a result of a different ionic makeup of the first and second fluid regions. The first and second fluids are in contact at a first substantially static interface. The sample material is electrophoresed through the first fluid region in the first channel portion toward the second fluid region concentrating the sample material at the first substantially static interface.

Another aspect of the present invention is a system for concentrating a material. The system comprises a first channel portion having a first fluid region and a second channel portion having a second fluid region. The first and second channel regions are connected at a first fluid junction. The first fluid region comprises the material and has a conductivity that is lower than the second fluid region. The first and second fluid regions are in contact at a first substantially static fluid interface. An electrical power supply is operably coupled to the first channel portion for applying an electric field through the first and second fluid regions in the first channel portion, to concentrate the material at the first substantially static interface.

BRIEF DESCRIPTION OF THE DRAWINGS

FIG. 5 illustrates the efficacy of the stacking methods of the present invention.

DETAILED DESCRIPTION OF THE INVENTION

I. General

Figure 1A:
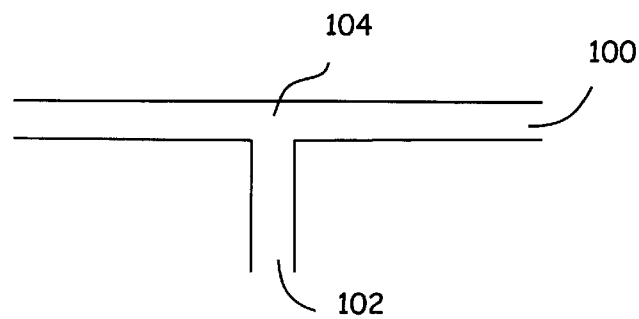
FIGS. 1A through 1E schematically illustrate the static interface stacking methods of the present invention and a simple device for carrying out such methods.
Figure 1B:
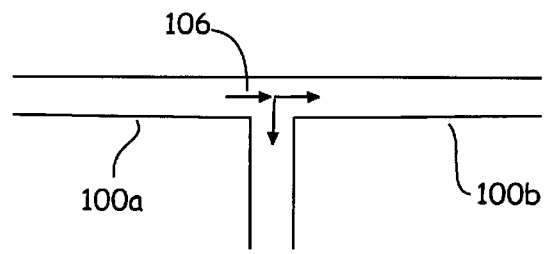
Figure 1C:
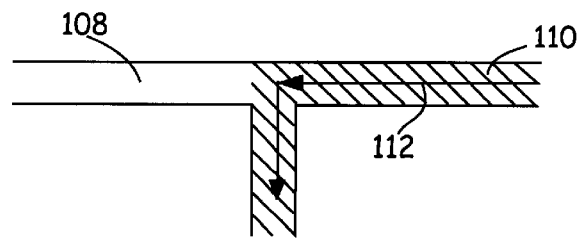
Figure 1D:
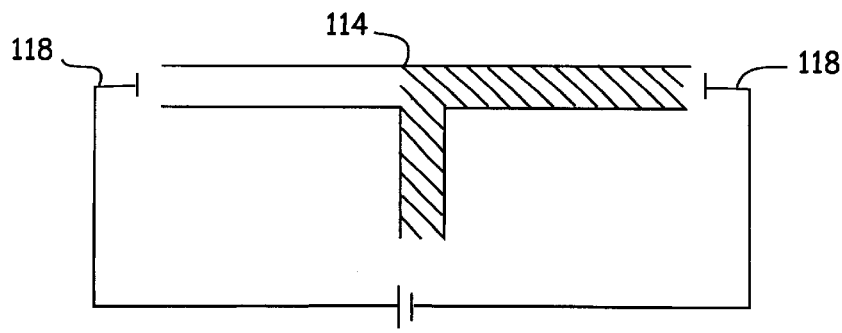
Figure 1E:
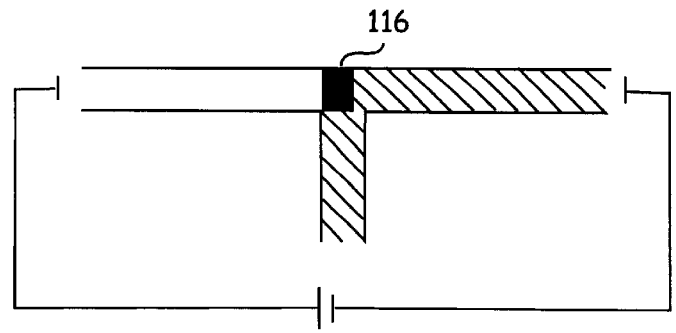

The present invention is generally directed to methods, devices and systems that operate in the microfluidic domain and that include the ability to concentrate, and sometimes, substantially concentrate a material of interest. In particular, the present invention is directed to methods of concentrating an analyte of interest at a substantially static fluid interface that is contained within a channel structure, and preferably, a microscale channel structure.

In general, the present invention provides for concentrating an analyte of interest by providing two fluid regions within a channel structure, through which the analyte of interest moves at different rates when subjected to a motive force, e.g., electrophoresis. The first fluid region abuts and interfaces with a second fluid region at a first substantially static fluid interface within the channel structure. The analyte of interest moves substantially faster through the first fluid region than through the second fluid region. By moving the material through the first fluid region toward the second channel region, one effectively concentrates the analyte at the interface of the two fluid regions, because that analyte substantially slows down when it reaches and crosses the interface into the second fluid region. This "stacking" effect results in a substantial concentration of the analyte at the interface. By combining this effect with the facility of controlled fluid/material movement through integrated channel networks in microfluidic devices, one can effectively concentrate, then further manipulate a particular material.

Sample stacking has been used routinely in conventional gel electrophoresis systems, where material in an aqueous solution is concentrated at an interface of the aqueous solution and a gel matrix by virtue of the analyte moving faster in the absence of a viscous gel matrix than in its presence. The present invention, in contrast, performs the concentration function without relying solely upon the velocity differences imparted on the analyte by the relative differences in permeability of a gel matrix and an aqueous solution within the channel.

For example, in one aspect, the present invention is directed to a method of concentrating a material, which comprises the first step of providing a first channel portion having at least first and second fluid regions disposed therein. The first fluid region includes the material in which the analyte of interest is contained. The analyte of interest has a greater velocity through the first fluid region than through the second fluid region. This greater velocity is typically a result of a greater electrophoretic velocity of the analyte through the first region than through the second region. In accordance with the present invention, and as distinguished from conventional gel electrophoresis methods, differences in electrophoretic velocity are preferably imparted by relative differences in the ionic make-up of the first and second fluid regions. By "different ionic make-up," is meant that the ionic concentrations and/or constituents of the first and second fluid regions differ to an extent sufficient to support differing electrophoretic velocities of the analyte when an electric field is applied through the fluid regions. As used herein, electrophoretic velocity refers to a measure of the linear velocity of a material that is caused by electrophoresis.

By way of example, the first region may be provided with a lower conductivity than the second fluid region as a result of it having lower ionic concentration, e.g., salts, buffers, etc. The lower conductivity results in a higher resistance cross this first fluid region than across the second fluid region. Because the resistance across the first region is greater than across the second fluid region, it will give rise to a greater voltage gradient. The greater the voltage gradient, the faster charged species will electrophorese. Once these charged species, e.g., the analyte of interest, reach the interface of the first and second fluid regions, it will slow down as a result of the smaller voltage gradient existing across the second fluid region. This results in a stacking of the analyte of interest at or near the interface.

Although described above with respect to differing conductivity/resistance, different ionic make-up also can include fluid regions of differing pH, which can result in a change in the net charge of an analyte of interest between the two regions. Specifically, the net charge on the analyte can change depending upon the difference between the pH of the fluid region and the isoelectric point (pI) of the analyte of interest. The further the pH of the fluid region is from the pI of the material of interest, the more charged the analyte will be. Also, whether the pH is above or below the pI will affect the nature of the net charge on the analyte, e.g., positive or negative. The change in relative charge on the analyte has a substantial effect on the electrophoretic mobility of that analyte. Specifically, a material that has a greater level of charge on it will electrophorese faster than the same material with a lesser or no charge on it. Additionally, the nature of the charge, will dictate the direction that the material will move within an electric field.

The present invention therefore provides devices, systems and methods for concentrating material within interconnected channel networks using the above described stacking phenomenon, and does so in a fashion that allows facile manipulation of the concentrated material.

II. Methods

A. Static Interface Concentration

As noted previously, in at least one aspect, the present invention is directed to methods of concentrating a material using the stacking phenomenon described above. The methods of the invention are generally carried out or provided within an interconnected channel structure, e.g., an integrated device that includes at least first and second channel portions that are in fluid communication at a first fluid junction, e.g., an intersection or common channel region. Two fluid regions are provided within the first channel portion, where one fluid region has a different ionic make-up than the second fluid region. The two fluid regions are in contact within the channel at a fluid interface.

The first fluid interface typically will not constitute a perfect interface but may represent some amount of diffusion between the two fluid regions. In addition, in accordance with the present invention, the first interface is substantially static within the channel structure. By "substantially static" is meant that during a particular concentration operation, the first fluid interface remains substantially within a relatively small channel region in the overall channel structure. Typically, a substantially static interface moves no more than 2 mm in either direction along a given channel region, preferably, no more than 1 mm in either direction, more preferably, no more than 500 $\mu$m in either direction, and in many cases, no more than 100 $\mu$m in either direction during a given concentration operation.

By providing the first fluid interface as substantially static, one can localize the benefits imparted by that interface, e.g., stacking-based concentration. In the case of concentrated material, the static interface may be located at a position at which a desired concentration is subjected to further manipulation or direction. For example, in some cases, the static interface may be positioned substantially at or adjacent to an inlet into a channel that intersects the main channel. Any material concentrated at the static interface is then readily directed into the connected channel for further manipulation and/or analysis, e.g., an electrophoretic separation. The phrase "positioned substantially at" is defined to mean that the interface is positioned with the same degree of specificity as used to describe the phrase "substantially static," namely that the interface is typically positioned within 2 mm of the intersection, preferably within 1 mm, more preferably within 500 $\mu$m and in many cases within 100 $\mu$m of the intersection of the second channel with the first channel.

Establishing the positioning of a static interface can be accomplished by a number of methods. For example, the two fluids that define the interface may be serially introduced into the first channel segment such that the interface is formed at the desired location. By way of example, a channel segment is first filled with the first fluid. The second fluid is then flowed into the first channel segment whereby it displaces the first fluid. This displacement is continued until the front of the second fluid, which is the fluid interface, reaches a desired position within the first channel.

This can be determined optically, e.g., visually, or using automated measuring systems including optical sensors which detect changes in the refractive index of fluids or other optical properties, e.g., presence of dyes. Alternatively, detection of the interface can be accomplished using electrochemical sensors, e.g., conductivity and/or pH sensors incorporated into the channel.

In preferred aspects, the interface is positioned substantially at an intersection of the first channel with a second channel, thereby allowing controlled flow of the first and second fluids up to and/or through the intersection, to define the interface substantially at the intersection. A simplified schematic illustration of this method of positioning the interface is illustrated in FIGS. 1A–1E. As shown in FIG. 1A, a first channel portion 100 and a second channel portion 102 are provided where the second channel portion intersects the first channel portion at a first fluid junction 104. In one aspect, both channel portions are filled with the first fluid 108 having the first ionic make-up, as described above. This is illustrated by the arrows 106 in FIG. 1B. The second fluid 110 is then flowed into a portion of the first channel 100, e.g., segment 100b, and into the second channel, as shown by arrows 112 in FIG. 1C, establishing an interface 114 where the two fluids contact each other.

Flow of the fluids through the channels is typically accomplished by applying either a positive pressure from the source of the flow or a negative pressure to the destination of the flow. The controlled flow of the second fluid 110 through the intersection is generally accomplished by applying a slight level of flow from channel portion 100a into the fluid junction 104, to prevent the second fluid from progressing into the channel portion 100a. Alternatively, physical barriers may be provided within channel portion 100a in order to prevent excessive fluid flow into the channel portion 100a from either of channel portion 100b or second channel 102. A particularly preferred physical barrier involves providing the channel portion 100a with a shallower depth as compared to he remainder of the channels or channel portions connected to the fluid junction 104. Typically, the channel portion 100a would be less than half the depth of the other channel portions, preferably less than one-fifth the depth of the other channels communicating at the fluid junction. Briefly, reduction of the channel depth results in a cube increase in the flow resistance in that channel, while only increasing electrical resistance, and thus electrophoretic movement of material, in a linear fashion. This allows the use of a formidable barrier to pressure based flow while not excessively altering the electrophoretic flow of material. This allows not only the set up of the fluid interface, but also facilitates maintaining that interface in a substantially static position.

In preferred aspects, however, the set-up and maintenance of the static interface is controlled through the controlled application of fluid flow through the channels that communicate at the fluid junction. Simultaneous control of fluid flows is generally controlled through the simultaneous application of pressure differentials through each of the channel segments. Systems and methods for such multi-channel pressure-based flow control are described in detail in U.S. patent application Nos. 60/184,390, filed Feb. 23, 2000, and 60/216,793, filed Jul. 7, 2000, each of which is hereby incorporated herein by reference in its entirety for all purposes. Briefly, such control utilizes a separate pressure based pump or pump outlet, e.g., a syringe or other positive displacement pump, operably coupled to an open terminus of each of the channel portions. Pressures are selectively applied and pressure feedback monitored to achieve the desired flow profile within and among the channels.

Once the substantially static interface between the first and second fluids is established within the first channel 100, the sample material to be concentrated is introduced into the first channel portion 100a. An electric field is then applied through the first and second fluid regions within channel portions 100a and 100b, respectively, e.g., via electrodes 118. The differential electrophoretic velocity of the sample material through the first and second fluids results in concentrated region of the sample material 116 substantially at the interface 114.

In the example illustrated in FIGS. 1A–1E, the concentrated material may ultimately be diverted into the second channel 102 for further manipulation or analysis. For example, the material may be combined with components of a biochemical system in a pharmaceutical candidate screen, or alternatively, it may be transported through a sieving matrix that is deposited in the second channel 102, to separate the material into its component species, e.g., electrophoretically.

The nature of the electric field applied through the first and second fluid regions, e.g., the direction and magnitude of current flow, is generally determined by the nature of the charge on the material that is to be concentrated, as well as the desired rate of concentration. For example for positively charged material, current is typically flowed (from a positive electrode to a negative electrode) through the first fluid region that includes the sample material, then into the second fluid region. Under this applied current, the positively charged sample material will move through the first fluid region toward the interface with the second fluid region. For negatively charged materials, a reverse current is typically applied, as negatively charged species will electrophorese in the opposite direction of current flow.

In the presence of the electric field, electroosmotic flow within the channel segment of interest is minimized by any of a number of means, including use of countervailing flow, e.g., pressure based, and/or masking of electroosmotic flow generating surface charges within the channels. These are described in greater detail below.

The level of concentration achievable using the methods described herein is primarily limited only by the ratio of the ionic content of the two fluid regions that contact at the first fluid interface. In the case of fluid regions having different conductivities, the first fluid typically has a conductivity that is more than 50% lower than the conductivity of the second fluid, preferably more than 80% lower than the second fluid, more preferably, more than 90% lower than the second fluid region, and in some cases more than 99% lower than the conductivity of the second fluid region, e.g., the conductivity of the first fluid region is less than 1% the conductivity of the second fluid region. Differences in ionic make-up will typically result in voltage gradients across the first fluid region that are at least twice, at least 5 times and even at least 10 times or even 100 times greater than across the second fluid region.

Practically speaking, concentrations of sample material that are at least 2 fold, 5 fold, 10 fold, 20 fold, 50 fold., 100 fold and more, over the concentration of the sample materially in the first fluid region can be achieved using the methods described herein.

B. Counter-Current Stacking

As an alternative to the static interface stacking methods described above, the present invention is also directed to methods of counter-current stacking and concentration. Countercurrent electrophoresis has been employed in the past as an avenue for enhancing separation efficiencies in capillary electrophoresis. In the present invention, however, a counter-current flow opposite to the direction of the electrophoretic flow is used to concentrate a sample material, which concentrated sample material may then be subjected to further manipulations.

The countercurrent methods of the invention employ bulk fluid flow within a channel segment in a first direction. An electric field is applied through the channel that gives rise to electrophoretic movement in the opposite direction. By adjusting the bulk fluid flow to precisely counter or nearly precisely counter the electrophoretic movement, one can affect a "piling-up" or stacking of electrophoretically moved sample material at a point at which the sample material enters into the bulk flowing fluid. Once a desired concentration is achieved, the concentrated material can be subjected to further manipulation, e.g., by introducing reagents into the bulk flowing stream, by redirecting the concentrated material out of the bulk flowing stream, or by stopping the bulk flow and further manipulating the sample material. Generally, bulk fluid flow may be accomplished by any of a variety of known methods, including application of pressure or vacuum to fluid filled channels, incorporation of micropumps and/or valves in channels, centrifugal fluid movement methods, gravity flow systems, wicking/capillary force driven systems and/or use of electrokinetic fluid movement methods, e.g., electroosmosis.

Figure 4A:
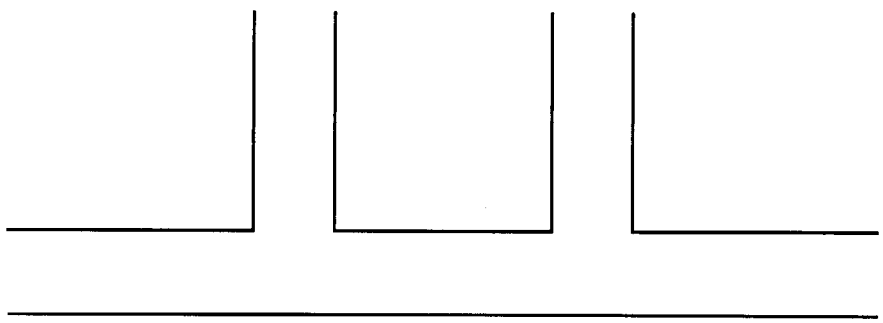
FIG. 4 schematically illustrates the counter-current concentration methods of the present invention and a simple channel configuration for carrying out such methods.
Figure 4B:
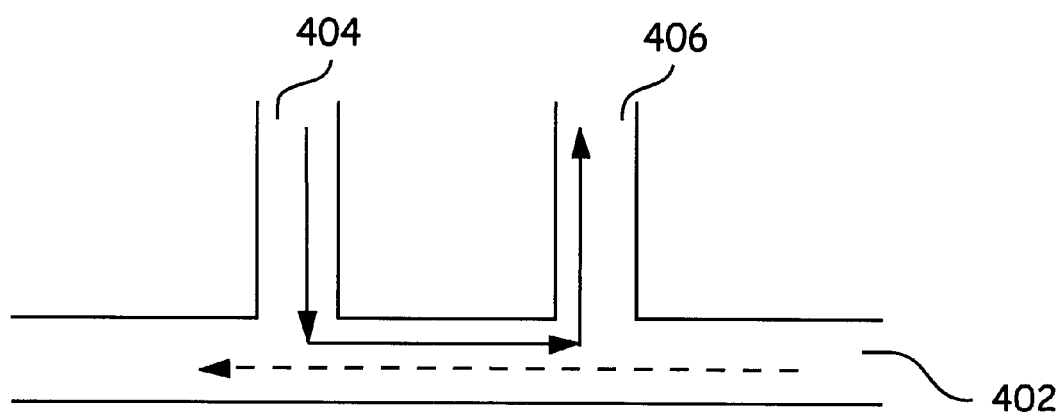

The counter current stacking methods of the present invention are schematically illustrated in FIGS. 4A and 4B. As shown in FIG. 4A, the methods employ a channel network 400 that includes a main concentration channel segment 402. Two channel segments 404 and 406 are provided in fluid communication with the main channel segment at either end of the concentration channel segment 402, and provide bulk fluid flow in a first direction as indicated by the solid arrows (shown in FIG. 4B). A second pair of channel segments 408 and 410 is also provided in fluid communication at opposing ends of the concentration channel segment 402 to provide electrophoretic movement (as shown by the dashed arrows) of charged species in the concentration segment 402 in the direction opposite that of the bulk fluid movement. The combination of bulk fluid flow in one direction and electrophoretic movement in the other direction results in an accumulation of charged species in channel segment 402. Once a desired level of concentration is achieved, one of the two motive forces, e.g., bulk or electrophoretic, is shut off, allowing the other force to predominate, driving the concentrated material out of channel segment 402. The concentrated material is then subjected to additional manipulations, e.g., as described above. The relative levels of electrophoretic or bulk fluid flow are provided using the same systems used in carrying out the static interface concentration aspects of the invention.

III. Devices

The present invention also includes devices that are useful in practicing the above-described methods. Briefly, the devices of the present invention include at least first and second channels, where the second channel intersects and is in fluid communication with the first channel at a first fluid junction that is positioned along the length rather than at a terminus of the first channel. Although described as first and second channels, it will be appreciated that such channels can be broken down and described in terms of multiple channel portions or segments, e.g., as illustrated in FIG. 1. By way of example, the first channel 100 shown in FIG. 1, includes two channel portions 100a and 100b that are in fluid communication at the first fluid junction 104.

A variety of different channel layouts can be used in conjunction with the present invention, from a simple two channel "T" junction, as shown in FIG. 1, to far more complex channel networks. The complexity and design of different channel networks is often dictated by the desired manipulations to the sample material prior and subsequent to the actual concentration step. A few exemplary channel network configurations are described below for purposes of illustrating the nature of the present invention.

In general, the channel containing devices of the present invention include a planar, layered structure that allows for microfabrication of the channel networks using conventional microfabrication technologies, e.g., photolithography and wet chemical etching of silica based substrates, and injection molding, embossing or laser ablation techniques of manufacturing in polymer substrates. Typically, channels are fabricated as grooves in a planar surface of a first substrate layer. A second substrate layer is then overlaid and bonded to the first substrate layer to cover and seal the grooves in the first layer to define sealed channels. Holes are typically provided in at least one of the substrate layers and are positioned so as to provide access ports or reservoirs to the channels that are disposed within the interior of the layered device. These ports or reservoirs provide access for introduction of fluids into the channels of the device, and also provide pressure ports or electrical access points for the channels of the device.

The devices of the invention also typically include first and second fluid regions disposed therein, where the first and second fluid regions are in contact at a substantially static, first fluid interface. This fluid interface is typically positioned substantially at the first fluid junction.

Figure 2A:
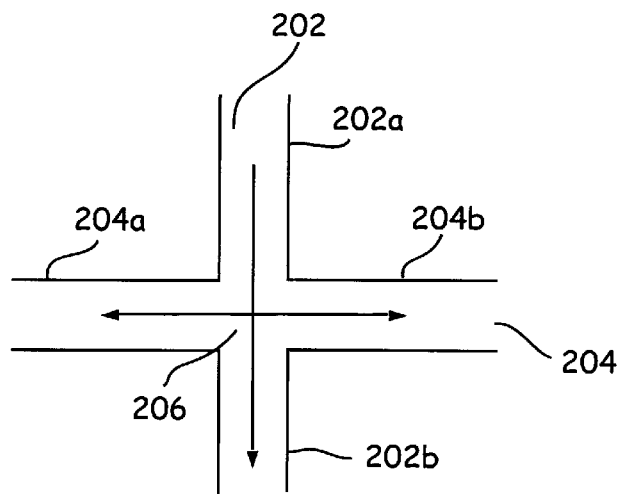
FIGS. 2A, 2B and 2C schematically illustrate one exemplary device structure for carrying out the static interface concentration methods of the invention.
Figure 2B:
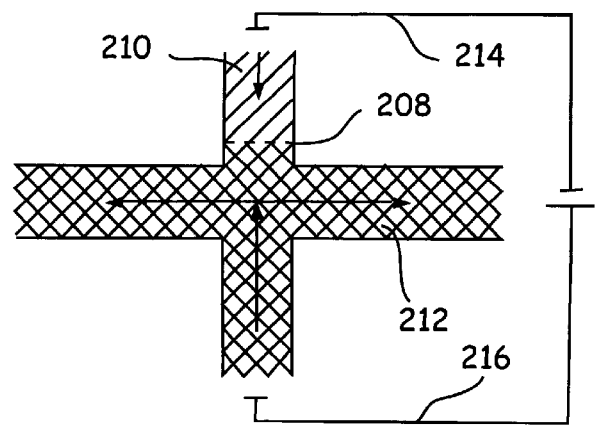
Figure 2C:
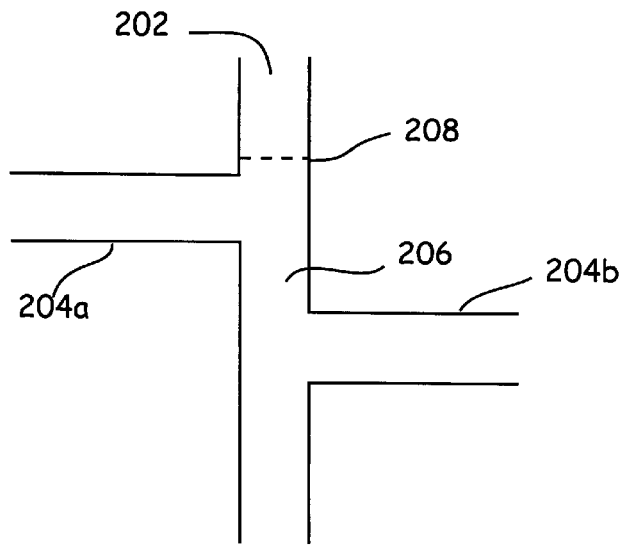

FIG. 2 illustrates a first exemplary device structure that employs the concentration function of the present invention. In particular, as shown in FIG. 2A, the device includes a channel geometry that comprises a simple crossing intersection, e.g., two channels 202 and 204, that cross each other and are in fluid communication at the intersection point or first fluid junction 206. This geometry is optionally described in terms of four channel segments (202a, 202b, 204a and 204b) communicating at a first fluid junction 206. In order to provide a larger area in which sample material could be concentrated, the fluid junction can be readily enlarged, e.g., by offsetting the point at which the cross channel segments (e.g., 202a and 202b) connect with the main channel 204. This configuration is illustrated in FIG. 2C.

FIG. 2B illustrates the channels including the static fluid interface 208, where the region 210 (indicated by hatching) has a first ionic make-up, e.g., relatively low conductivity, and the region 212 (indicated by cross-hatching) has a second ionic make-up, e.g., relatively high conductivity. In order to establish the fluid interface, all of the channel segments 202a and b and 204a and b, that communicate at the first fluid junction 206 are filled with the first fluid 210. The second fluid 212 is then transported into all but one of these channel segments by, e.g., pumping the second fluid into the fluid junction 206 through channel segment 204a, and controlling the flow at the junction 206 such that the second fluid only flows into segments 202b and 204b. This yields the channel network shown inn FIG. 2B with a static fluid interface 206 in the position indicated therein. Alternatively, the entire channel structure can be first filled with the second fluid. The first fluid is then introduced into the sample loading channel segment, e.g., channel segment 202a, and advanced until the fluid interface reaches the desired position.

With respect to the channel layout illustrated in FIG. 2C, establishment of the static fluid interface is accomplished in substantially the same fashion as done in FIG. 2B. Specifically, in preferred aspects, all of the channel segments are filled with the first fluid. The second fluid is then loaded into all but the sample loading channel segment, e.g., 202a, by introducing the second fluid into one of the other channel segments, e.g., segment 204a, and allowed to flow through all but the loading channel 202a by controlling flow at the fluid junction 206. Again, in an alternative method, all of the channels are filled with the second fluid and the first fluid is introduced into a single channel segment, e.g., 202a, and advanced until the interface of the first and second fluids reaches the desired position.

Maintaining the fluid interface at a static or substantially static location can be accomplished by a number of methods or combinations of methods, as noted above, whereby bulk fluid flow through the location of the static interface is eliminated or substantially eliminated. In a microfluidic system that utilizes electrokinetic transport, bulk fluid flow can originate from a number of sources. First, bulk fluid flow may originate from hydrostatic pressure gradients that exist across the length of a channel segment, forcing bulk fluid flow therethrough. Such hydrostatic pressure gradients may be caused by elevated fluid levels at one end of a channel versus the other end of the channel, by capillary forces that draw fluid toward one end of a channel, by the existence of elevated pressures at one end of a channel versus the other end of the channel, and the like. In electrokinetic systems, bulk fluid flow can also be caused by electroosmotic movement of fluid within the channel. Briefly, where a channel has a charged interior surface, application of an electric field across an aqueous fluid disposed within that channel can cause bulk fluid movement through that channel under the appropriate conditions. See, e.g., U.S. Pat. No. 5,858,195.

Elimination of hydrostatic fluid flow is simply accomplished by eliminating or counteracting the pressure differentials that exist across the channel segment of interest. This may be done by eliminating fluid height differences at opposing ends of channels or by tuning pressures that are applied at one or both opposing channel ends such that there is no bulk fluid movement within the channels.

Elimination of electroosmotic flow can be accomplished by several means as well. In preferred aspects, the electroosmotic flow is eliminated by masking the charge that exists on the channel's interior surface, such that it cannot give rise to EO flow. Charge masking may be accomplished through the chemical treatment of the channel prior to its use, addition of dynamic coatings to the channel, which coating associate with the surface to mask charges, adjustment of the fluid properties, e.g., the fluid pH so as to eliminate any effective surface charge in the channel, and/or the addition of viscosity increasing elements within the channel such that viscous resistance to flow counteracts any EO flow. In particularly preferred aspects, dynamic coatings are used in the channel segments of interest which both associate with the surface of the channel, and increase the viscosity of the fluid. These dynamic coatings have the additional advantage of providing sieving matrices for macromolecular separations. Particularly preferred dynamic coatings include, e.g., linear polymers, i.e., linear polyacrylamides, dimethylacrylamides and charged derivatives thereof (see, U.S. Pat. No. 5,948, 227). In addition to the use of dynamic coatings, in preferred aspects, bulk flow is also controlled by tuning pressures at opposing ends of channels, such that any fluid flow is substantially eliminated. In addition, as noted above, providing different channel segments with different depths also serves to control relative levels of fluid flow within interconnected channel, e.g., substantially reducing bulk fluid flow without substantially reducing electrophoretic material movement.

Once the static interface is established in the device shown in FIG. 2, a sample material is introduced into the first fluid region 210 which has, e.g., a lower conductivity than the second fluid region 212. This is typically accomplished by introducing the sample material into channel segment 202a via an associate reservoir (not shown), e.g., that is disposed at the unintersected terminus of segment 202a. A first electric field is then applied through the first fluid region in channel segment 202a and through the second fluid region within channel segment 202b, e.g., via electrodes 214 and 216 schematically represented in FIG. 2B. This electric field causes the electrophoresis of sample material in channel segment 202a toward the fluid interface 208. Once the sample material crosses the interface 208, its electrophoretic velocity is substantially reduced by the different ionic content of the second fluid region 212. This slowed velocity results in a concentration or stacking of the sample material at or just past the interface in the second fluid region.

Once a desired concentration has been achieved at the static interface, the concentrated material can then be subjected to additional manipulations. In the case of the device shown, an exemplary further manipulation is to redirect the concentrated material into a separation channel, e.g., channel segment 204b, in which there is disposed a separation matrix, e.g., a dynamic coating as described above that is disposed throughout the channel network. Redirection of the concentrated material typically involves shifting the primary electric field from through channel 202 to through channel 204 such that the concentrated material moves from the intersection or fluid junction 206 into channel segment 204b. Additional electric fields may exist in order to push back any additional material that is in channel 202, to prevent leakage of that material from smearing the separations in channel 204b. Similarly, during concentration, additional electric fields may be applied to constrain or pinch the concentrated plug within the fluid junction. Use of pinching and pull-back fields in an interconnected channel network is described in detail in U.S. Pat. No. 5,858,195, which is incorporated herein by reference in its entirety.

As the concentrated material is electrophoretically moved through the separation matrix in channel segment 204b, it is separated into bands of is constituent elements, e.g., different sized nucleic acids. The separated bands are then detected at a position along channel segment 204b or a connected channel, e.g., by virtue of a label associated with the sample material. Because the sample material was more concentrated upon injection into the separation channel, it results in a higher concentration within each of the separated bands, thus rendering those bands more easily detectable.

FIG. 3 schematically illustrates a more complex channel geometry for carrying out the concentration methods described herein. In particular, the channel layout 300 includes sample loading channel segments, e.g., 302a and 302b, that are connected to channel segments 304a and 304b connected to each other by a fluid junction 306 (here shown as channel segment 306). An additional channel segment 302c is provided connected to the fluid junction 306, in order to provide an additional source for the second fluid, e.g., the high conductivity buffer, to provide facilitated set-up of the static interface (see below). In particular, the channel configuration functions substantially as described for FIG. 2C, except that the second fluid is provided within channel 302c, as well as in channel segment 304a and 304b. The sample material in channel segment 302a is then subjected to an electric field whereby the sample material is concentrated in the second fluid region in the fluid junction 306. The concentrated material is then directed down channel segment 304b for further manipulation, in the same fashion described above.

Figure 3A:
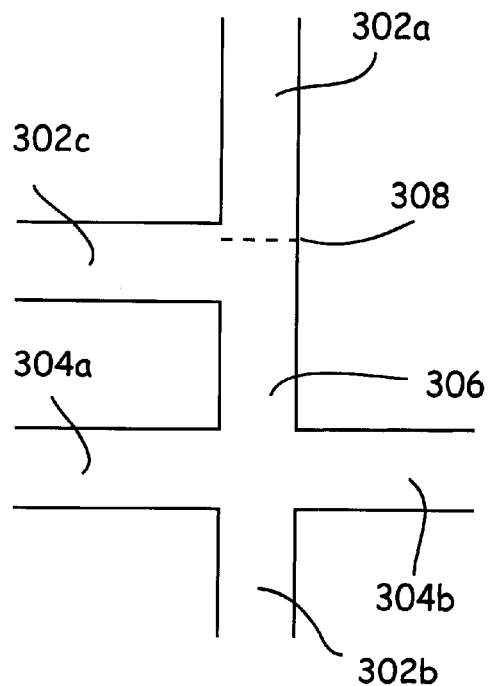
FIG. 3 schematically illustrates an alternate channel configuration for use in the static interface concentration methods of the present invention.
Figure 3B:
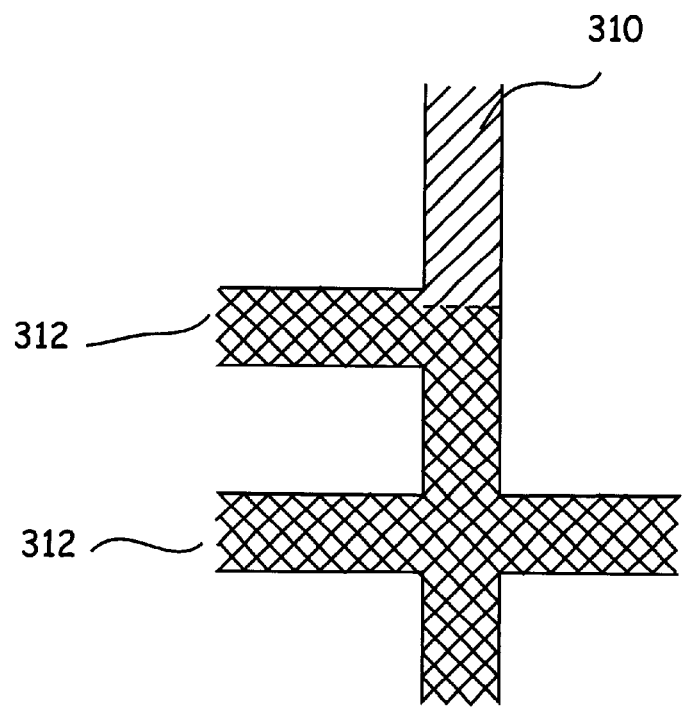

In providing an additional high conductivity buffer source channel, e.g., channel 302c, set-up of the static interface is facilitated in the channel network shown in FIG. 3A. This set-up is shown schematically in FIG. 3B. In particular, as shown, the entire channel network is first filled with the first fluid 310, e.g., low ionic strength, which is indicated by hatching. The second fluid 312 (indicated by cross-hatching) is then simply directed through channel 302b, 304a, 304b and 304c. Again, control of flow at the fluid junction is a simple matter of regulating flow in the various channels that are connected at that junction, e.g., by flowing the second fluid in through channels 304a and 304c. A slight level of flow is also optionally applied through channel 302a, in order to prevent movement of the fluid interface 308. Following this set-up, the main static interface 308 will be established at the fluid junction 306. Sample material is then electrophoresed from sample channel 302a (and optionally, 302c) into the fluid junction 306, where it will concentrate just beyond the static interface 308. The concentrated material is then optionally transported into a connected channel segment, e.g., 304b, for additional manipulation or analysis.

FIG. 4 schematically illustrates a channel structure useful for carrying out the countercurrent concentration methods of the present invention. Like the static interface methods described above, these countercurrent methods rely upon a shift in velocity of the sample material in one channel segment in order to accomplish the desired concentration. In these methods, however, the velocity shift is due primarily to the counter directional bulk fluid flow, e.g., counter to the direction of electrophoretic movement. As shown in FIG. 4A, a main channel 402 is provided, with two side channels 404 and 406 intersecting main channel 402 at two discrete points. The main channel is coupled to a pressure source or other bulk flow system, e.g., electroosmotic pressure pump, pressure or vacuum pump, manifold, etc., or the like. The side channels are each coupled to an electrical power supply, e.g., via electrodes 416 and 418, for applying an electric field through channels 404 and 406, via channel segment 402a.

In operation, as shown in FIG. 4B, fluid is bulk flowed through channel 402 in a first direction, e.g., as shown by the dashed arrow. Sample material is then electrophoretically introduced into channel 402 from side channel 404 toward channel 406, in the direction opposite the bulk fluid flow, as shown by the solid arrow. The magnitude of the electrophoretic velocity is, as noted, just sufficient to negative or slightly overcome the magnitude of the velocity of bulk flow that is in the opposite direction of the bulk flow. Thus, the electrophoretic velocity through the moving fluid in the main channel is the same as or slightly greater than the absolute velocity of the fluid itself.

Once the sample material reaches the flowing stream in channel 402, it is slowed to a point where it builds up within channel 402, e.g., in segment 402a. The bulk flow and electrophoretic flow of sample material are selected so as to allow the sample material to flow into channel segment 402a and not be swept out by the bulk flow. Typically, the bulk fluid velocity is slightly less than the electrophoretic velocity of the sample material in the absence of the bulk flow. This allows an accumulation of sample material in channel segment 402a. Once a desired level of concentration is achieved, the concentrated material is then moved into a connected channel, e.g., segment 402b or 402c, for further manipulation or analysis. Moving the sample material into a connected channel segment typically involves switching off the electrophoretic flow, e.g., by removing the electric field, such that bulk flow drives movement of the sample material out of channel segment 402a, or by switching the direction of the bulk flow.

IV. Systems

In order to operate the devices of the invention in accordance with the methods of the invention typically requires additional control elements, e.g., for driving fluid movement and electrokinetic forces within the channels of the device, and optionally for maintaining a static fluid interface within the device. While these elements can be incorporated into the device itself, the interest in low cost, flexible devices and applications typically warrants including these elements in an overall system of which the device is a removable and disposable part. In particular, the devices of the invention are typically removably mounted upon and interfaced with a control or base unit that includes electrical power supplies as well as pressure based flow systems, e.g., pumps and optional switching manifolds, as well as an appropriate interface for the device that is being used. An example of such systems is described in U.S. Pat. No. 5,955,028, which is incorporated herein by reference in its entirely for all purposes.

In addition to control aspects, the overall system also optionally includes a detector for monitoring the progress of the analysis that is being carried out. Typically, such detectors are selected from optical detectors, e.g., epifluorescent detectors, electrochemical detectors, e.g., pH sensors, conductivity sensors, and the like, and thermal sensors, e.g., IC thermal sensors, thermocouples, thermistors, etc. These detectors are also appropriately interfaced with the device when it is placed in the system, e.g., via a detection window in the device for optical signals, or via a sensor that is incorporated within the channels of the device and coupled to the system via an appropriate electrical connection.

In particularly preferred aspects, the controller instrumentation includes both pressure and/or vacuum sources, as well as electrical power supplies, all of which are coupled to appropriate interfaces for operably connecting those pressure/vacuum sources to a microscale channel network, so as to permit electrophoretic concentration of sample material and allow bulk fluid control, e.g., movement or reduction of movement.

V. Examples

The invention is further illustrated with reference to the following non-limiting examples:

A microfluidic device containing a simple cross-intersection channel network, e.g., four channel segments communicating with a single fluid junction point, was provided in a glass substrate. The channels were treated with polydimethylacrylamide (PDMA) or polyethylene glycol (PEG) to eliminate or substantially reduce electroosmotic flow.

The unintersected termini of the channel segments were connected to fluid reservoirs in the surface of the devices. Two buffers were prepared. The high conductivity buffer was 100 mM HEPES with 200 mM NaCl, while the low conductivity buffer was 0.5 mM HEPES with 1 mM NaCl. Due to impurities and other contamination, the conductivity ratio of these two buffers was about 140:1 instead of the expected 200:1.

Two dyes, a fluorescein sodium salt and a fluorescein labeled polypeptide, at approximately 5 $\mu$M, were mixed into the low conductivity buffer, to serve as detectable charged sample materials. The entire channel network was filled with the low conductivity buffer by placing that buffer into one reservoir and allowing it to wick throughout the channel network. High conductivity buffer was then placed in the remaining three reservoirs. The chip was then placed into a multiport pressure controller interface, which simultaneously controls the pressure applied at each of the four reservoirs. By knowing the channel geometry and viscosity of the buffers, one can calculate the required pressures to achieve the desired flow rates (see Provisional U.S. Patent Application Nos. 60/184,390, and 60/216,793, which were previously incorporated by reference). The system flowed the high conductivity buffer through two of the channel segments into the intersection and out through a third channel segment while applying a slight flow in from the fourth channel to maintain the low conductivity buffer interface. This resulted in high conductivity buffer in three of the four channels and low conductivity buffer in the fourth channel, with the interface between the two buffers immediately adjacent to the intersection. A similar approach would also be used in more complex channel networks.

After preparing the static interface in the four channel segment network, an electric field was applied through the low conductivity buffer and at least one of the high conductivity channels. The field caused a substantial concentration of the charged fluorescein dye at the interface between the low and high conductivity buffer regions, as observed visually. In a typical experiment, increases in concentration of about a factor of 100 was observed (as determined from recorded dye intensity). This agreed closely with the theoretical prediction of 140×concentration based upon the conductivity ratio between the fluid regions.

Figure 5A:
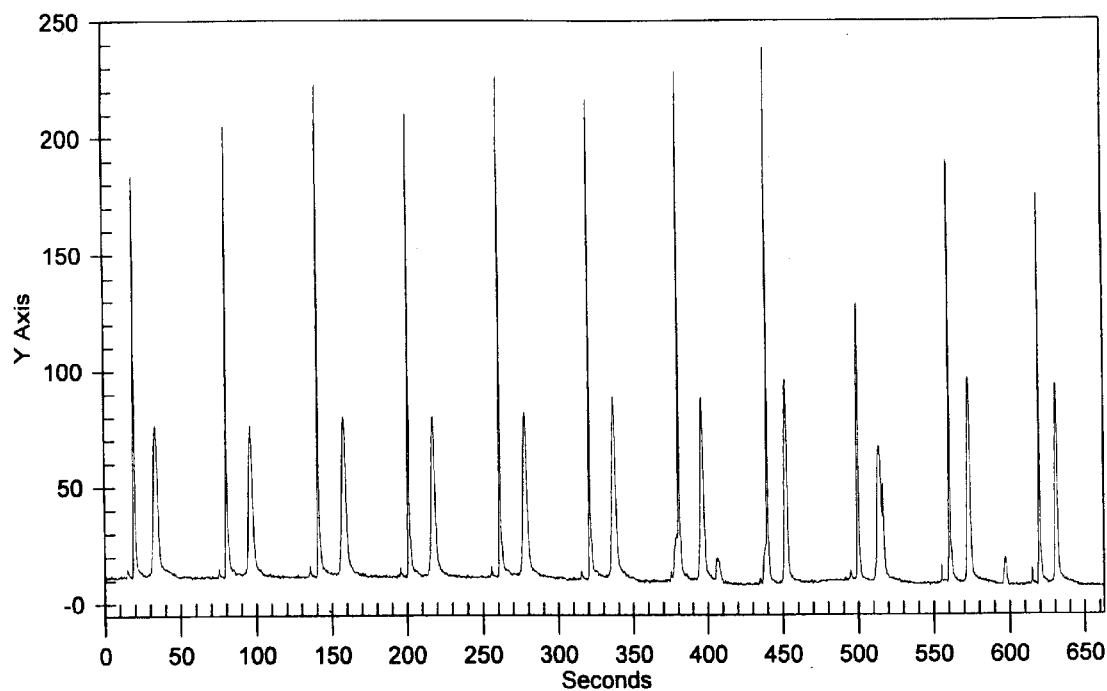
FIG. 5A illustrates an electropherogram of the separation of two dye materials when no stacking was used.
Figure 5B:
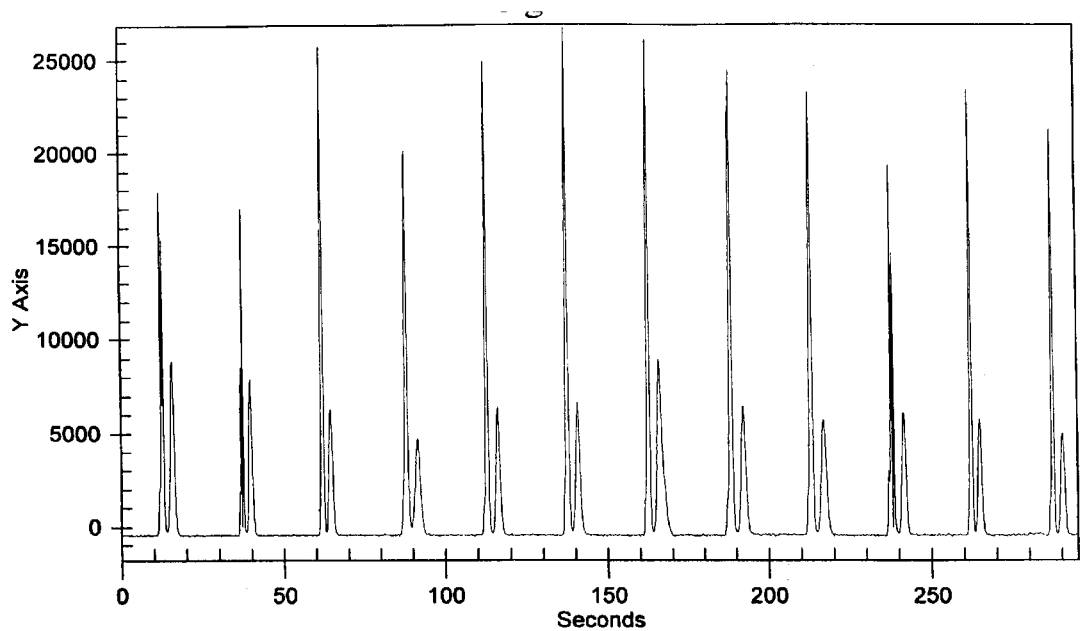
FIG. 5B illustrates an electropherogram of the same two dye peaks following use of the static interface stacking methods of the invention.

The concentrated material was then injected into a connected channel for separation by switching the applied electric fields. FIG. 5A shows an electropherogram for the separation of the two dye materials when no stacking was used. FIG. 5B illustrates the same two dyes separated following stacking in accordance with the present invention. As can be seen from these two figures, the fluorescent intensity of the separated peaks that had been subjected to the stacking methods of the invention increased by approximately 100 fold.

Unless otherwise specifically noted, all concentration values provided herein refer to the concentration of a given component as that component was added to a mixture or solution independent of any conversion, dissociation, reaction of that component to a alter the component or transform that component into one or more different species once added to the mixture or solution.

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

What is claimed is:

1. A method of concentrating a material, comprising:
providing a first channel portion having at least first and second fluid regions disposed therein, the material having a first electrophoretic velocity in the first fluid region, and having a second electrophoretic velocity in the second fluid region, wherein the second electrophoretic velocity is less than the first electrophoretic velocity as a result of a different ionic make up of the first and second fluid regions, the first and second fluid regions being in contact at a first substantially static interface; and electrophoresing the sample material through the first fluid region in the first channel portion toward the second fluid region, the sample material concentrating at the first substantially static interface.

2. A method of concentrating a material, comprising:
providing at least first and second channel portions, wherein the second channel portion intersects and being in fluid communication with the first channel portion, the first channel portion having at least first and second fluid regions disposed therein, the first fluid region comprising the material and having a conductivity that is lower than the second fluid region, the first and second fluid regions being in contact at a first substantially static interface; and
applying an electric field through the first and second fluid regions in the first channel portion to concentrate the material at the first substantially static interface.

3. The method of claim 2, wherein the first static interface is provided substantially at a first fluid junction between the first channel portion and the second channel portion.

4. The method of claim 3, wherein at least the second channel portion is provided with a separation matrix disposed therein.

5. The method of claim 3, wherein the third channel portion is in fluid communication with the first channel portion substantially at the first fluid junction.

6. The method of claim 3, further comprising providing a fourth channel portion in fluid communication with the first channel portion.

7. The method of claim 3, wherein the material comprises nucleic acids.

8. The method of claim 3, wherein the material comprises polypeptides.

9. The method of claim 3, wherein the material comprises a negatively charged micellar formulation.

10. The method of claim 3, wherein an interior surface of the first channel portion is treated to reduce a zeta-potential of the surface.

11. The method of claim 3, wherein the first channel portions comprises a surface coating which masks a surface charge within the first channel portion.

12. The method of claim 3, wherein the first channel portion comprises a dynamic coating material disposed therein.

13. The method of claim 3, wherein the substantially static fluid interface is maintained substantially at the first fluid junction.

14. The method of claim 3, further comprising the step of moving the material concentrated at the first fluid interface into the second channel portion.

15. The method of claim 3, wherein the material is moved into the second channel portion electrokinetically.

16. The method of claim 3, wherein the material is moved into the second channel portion electrophoretically.

17. The method of claim 3, wherein the providing step further comprises providing a third channel portion in fluid communication with the first and second channel portions at the first fluid junction.

18. The method of claim 3, wherein the substantially static fluid interface is maintained substantially at the first fluid junction.

19. The method of claim 2, further comprising providing a third channel portion in fluid communication with the first channel portion.

20. The method of claim 2, wherein the material is positively charged.

21. The method of claim 2, wherein the material is negatively charged.

22. The method of claim 2, wherein the material is provided in a mixture of different materials.

23. The method of claim 2, wherein the applying step comprises applying an electric field of a sufficient size and for a sufficient duration to concentrate the material at least 2 fold.

24. The method of claim 2, wherein the applying step comprises applying an electric field of a sufficient size and for a sufficient duration to concentrate the material at least 5 fold.

25. The method of claim 2, wherein the applying step comprises applying an electric field of a sufficient size and for a sufficient duration to concentrate the material at least 10 fold.

26. The method of claim 2, wherein the applying step comprises applying an electric field of a sufficient size and for a sufficient duration to concentrate the material at least 100 fold.

27. The method of claim 2, wherein the step of providing the comprises maintaining the first static interface in position by applying pressure to at least one of the first and second fluid regions to maintain the first static interface in a substantially static position within the first channel portion.

28. The method of claim 2, wherein during the applying step, there is substantially no electroosmotic flow in the first channel portion.

29. The method of claim 2, wherein the second channel portion is in fluid communication with the first channel portion at a first fluid junction.

30. The method of claim 2, wherein the first conductivity is more than 10% lower than the second conductivity.

31. The method of claim 2, wherein the first conductivity is more than 20% lower than the second conductivity.

32. The method of claim 2, wherein the first conductivity is more than 50% lower than the second conductivity.

33. The method of claim 2, wherein the first conductivity is more than 75% lower than the second conductivity.

34. The method of claim 2, wherein the first conductivity is more than 90% lower than the second conductivity.

35. The method of claim 2, wherein in the applying step, a voltage gradient across the first fluid region is at least twice as great as a voltage gradient across the second fluid region.

36. The method of claim 2, wherein in the applying step, a voltage gradient across the first fluid region is at least 5 times greater than a voltage gradient across the second fluid region.

37. The method of claim 2, wherein in the applying step, a voltage gradient across the first fluid region is at least 10 times greater than a voltage gradient across the second fluid region.

* * * * *